United States Patent [19]

Wise et al.

[11] 4,061,636
[45] Dec. 6, 1977

[54] NAPHTHALENONE PHTHALAZINYLHYDRAZONES

[75] Inventors: Lawrence D. Wise, Denville; Glenn C. Morrison, Randolph, both of N.J.

[73] Assignee: Warner-Lambert Company, Morris Plains, N.J.

[21] Appl. No.: 657,436

[22] Filed: Feb. 12, 1976

[51] Int. Cl.² .............. C07D 237/34; C07D 413/12; A61K 31/50
[52] U.S. Cl. .............. 260/250 P; 424/250; 424/248.56; 544/116
[58] Field of Search .................. 260/250 P

[56] References Cited
U.S. PATENT DOCUMENTS

| 3,274,185 | 9/1966 | Segal et al. | 260/250 P |
| 3,840,539 | 10/1974 | Ueno et al. | 260/250 P |

OTHER PUBLICATIONS de Cat et al; Chem. Abs., vol. 45:10249f (1950).
Burger; Med. Chem., 2nd Ed., p. 497 (1960).
Burger; Med. Chem., 3rd Ed., p. 1588 (1970).

Primary Examiner—Donald G. Daus
Assistant Examiner—Mary C. Vaughn
Attorney, Agent, or Firm—Albert H. Graddis; Frank S. Chow

[57] ABSTRACT

Naphthalenone phthalazinylhydrazones of the formula:

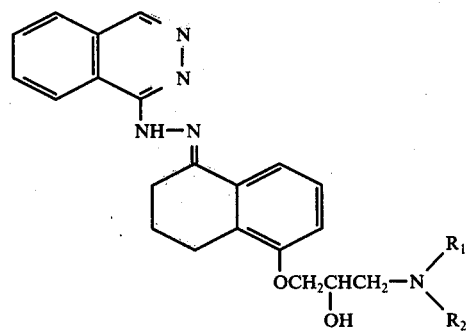

are disclosed. In the above formula $R_1$ is hydrogen or alkyl, $R_2$ is alkyl, preferably branched alkyl, or N, $R_1$ and $R_2$ taken together forming a heterocyclic ring. These compounds are useful as antihypertensive agents.

6 Claims, No Drawings

NAPHTHALENONE PHTHALAZINYLHYDRAZONES

The present invention relates to compositions of matter and, more particularly, it relates to naphthalenone phthalazinylhydrazones having the following structural formula:

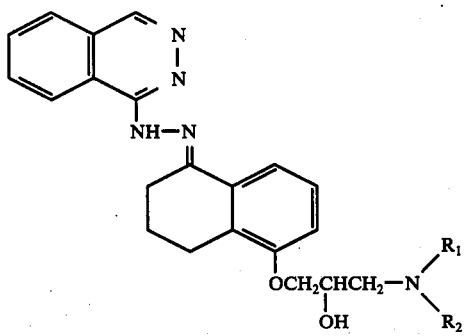

wherein $R_1$ is hydrogen or alkyl of 1-6 carbon atoms such as, for example, methyl, ethyl, propyl, isopropyl, butyl, isobutyl and the like; $R_2$ is alkyl of 1-6 carbon atoms, preferably branched alkyl of 3-6 carbon atoms such as, for example, isopropyl, isobutyl, sec-butyl, tert-butyl and the like; or N, $R_1$ and $R_2$ taken together forming a heterocyclic ring having a maximum of 8 carbon atoms such as, for example, pyrrolidine, piperidine, morpholine and the like.

Also embraced within the scope of this invention are the corresponding pharmaceutically acceptable acid addition salts of the above compounds, their quaternary ammonium salts and N-oxides.

The above compounds exhibit hypotensive activity in a mammalian host. For example, in a test conducted according to the method of Wise, et al., *J. Med. Chem.*, 17: 1232 (1974) these compounds were found to exhibit a prolonged hypotensive action of spontaneously hypertensive rats at an oral dosage of about 10-30 mg/kg. Moreover, when compared to hydralazine, a well-known antihypertensive agent, these compounds were found to exhibit a more gradual onset of hypotensive activity and did not cause undesirable side effects such as reflux tachycardia.

The compounds of this invention, including their pharmaceutically acceptable acid addition salts, the quaternary salts and the N-oxides are indicated in the management of mild or essential hypertension in human beings or animals. Generally speaking, a dose of 10-25 mgs three or four times daily is indicated for the management of hypertension. As with any hypotensive agent, the dosage regimen may be adjusted according to individual response by methods well known in hypertensive therapy.

In order to use these compounds as well as their salts or N-oxides, they are formulated into dosage forms such as tablets by combining with diluents such as lactose and mannitol, employing standard tabletting technology.

For parenteral administration, an aqueous solution of the acid addition salt is formulated by standard pharmaceutical technology.

According to the present invention, Compound I is prepared by treating hydralizine of the formula:

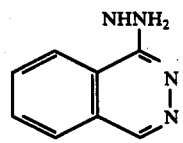

with a compound of the formula:

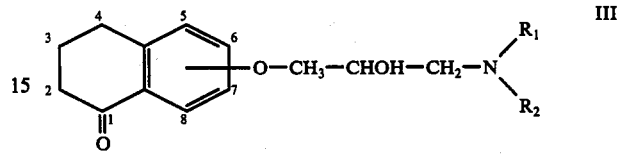

Generally speaking, the reactants are refluxed together in an inert solvent such as lower alkanoyl. The desired reaction product is recovered in the form of a precipitate which may be purified by the recrystallization technique.

Starting Compound II is prepared according to the procedure described in U.S. Pat. No. 2,484,029, whereas starting Compound III is prepared according to the procedure described in U.S. Pat. No. 3,641,152 and U.S. Pat. No. 3,649,691.

In order to enhance the therapeutic spectrum, the compounds of this invention may also be combined with other therapeutic agents. These include, for example, sedatives such as phenobarbital, diuretics such as etozolin, etozolinic acid, chlorothiazide, hydrochlorothiazide, and the like.

As will become obvious to those skilled in the art, starting Compound III occurs in optical isomers, i.e., having D or L configuration, or the corresponding racemic mixtures. Consequently, depending on the nature of starting Compound III, the resulting Compound I of this invention will have the optical configuration corresponding to Compound III.

Among the pharmaceutically acceptable acid addition salts there may be mentioned, for example, the hydrochloride, the nitrate, the sulfate, and phosphate salts. The quaternary ammonium salts include, for example, the corresponding iodide and bromide salts. These salts are prepared by treating the free base with the corresponding acid or alkyl ammonium halide. The N-oxides are prepared by treating Compound I with an oxidizing agent such as, for example, hydrogen peroxide.

The following examples are included to illustrate the present invention. All temperatures are given in degrees Centigrade.

EXAMPLE 1

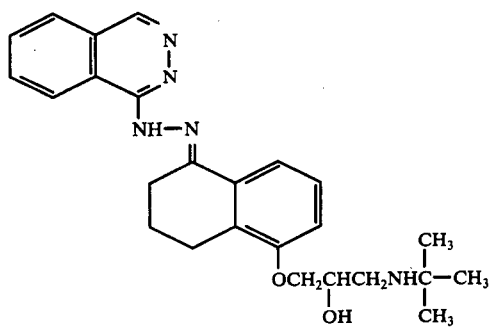

L-5-{[3-(1,1-dimethylethyl)amino]-2-hydroxypropoxy}-3,4-dihydro-1(2H)-naphthalenone (1-phthalazinyl)-hydrazone. A solution of 12.0g of L-5-{[3-(1,1-dimethylethyl)amino]-2-hydroxypropoxy}-3,4-dihydro-1(2H)-naphthalenone and 6.60g of 1-hydrazinophthalazine in 100ml of ethanol was refluxed for 48 hours. The reaction mixture was cooled, and water was added. The resulting precipitate was collected and dried to afford 12.4g (69.7%) of yellow powder, mp. 156°–158°. The product was recrystallized twice from ethanol to give yellow crystals, mp. 155°–156°.

Anal. Calcd. for $C_{25}H_{31}N_5O_2$: C, 69.25; H, 7.21; N, 16.16. Found: C, 69.42; H, 7.27; N, 16.13.

EXAMPLE 2

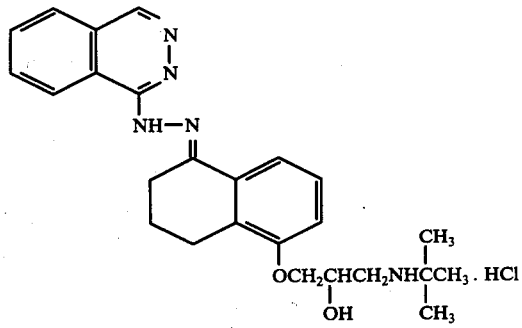

D,L-5-{[3-(1,1-Dimethylethyl)amino]-2-hydroxypropoxy}-3,4-dihydro-1-(2H)-naphthalenone (1-phthalazinyl)-hydrazone hydrochloride. A solution of 10.0g of D,L-5-{[3-(1,1-dimethylethyl)amino]-2-hydroxypropoxy}-3,4-dihydro-1(2H)naphthalenone hydrochloride and 4.85g of 1-hydrazinophthalazine in 15ml of ethanol was refluxed for 4 hours. A thick yellow solid slowly precipitated. The mixture was cooled, and the solid was collected to yield 10.4g (78.8%) of yellow powder, mp. 273°–275° dec. Recrystallization of the product from methanol-ether gave yellow crystals, mp. 281°–283° dec.

Anal. Calcd. for $C_{25}H_{31}N_5O_2 \cdot HCl$: C, 63.89; H, 6.86; N, 14.90; Cl, 7.54. Found: C, 63.86; H, 6.88; N, 14.89; Cl, 7.64.

EXAMPLE 3

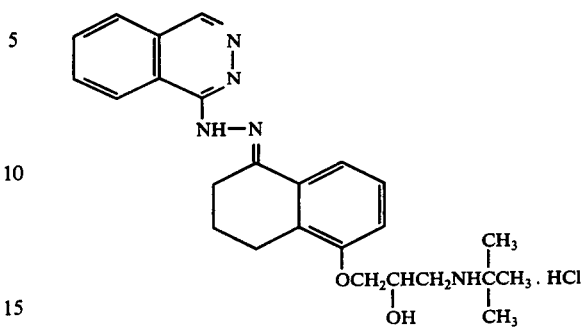

D-5-{[3-(1,1-Dimethylethyl)amino]-2-hydroxypropoxy}-3,4-dihydro-1(2H)-naphthalenone (1-phthalazinyl)-hyrazone hydrochloride. A mixture of 12.4g of D-5-{[3-(1,1-diethylethyl)amino]-2-hydroxypropoxy}-3,4-dihydro-1(2H)-naphthalenone and 8.40g of 1-hydrazinophthalazine hydrochloride in 150ml of ethanol was refluxed for 3 hours. The original solid slowly dissolved, and a new precipitate formed. The mixture was cooled to room temperature after which the solid was collected and dried to give 16.4g (81.5%) of yellow powder, mp. 260°–264° dec. Recrystallization of the product from methanol afforded an analytical sample, mp. 278°–280° dec.

Anal. Calcd. for $C_{25}H_{31}N_5O_2 \cdot HCl$: C, 63.89; H, 6.86; N, 14.90; Cl, 7.54. Found: C, 63.84; H, 6.78; N, 14.79; Cl, 7.74.

EXAMPLE 4

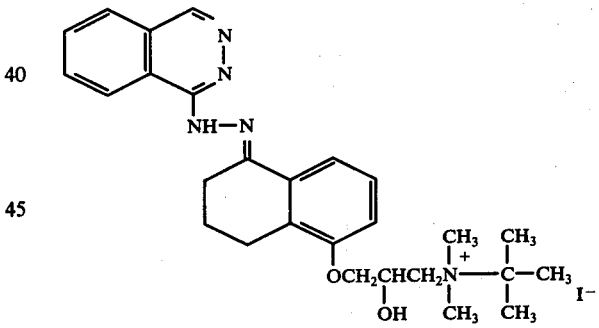

D,L-(1,1-Dimethylethyl)[2-hydroxy-3-({5,6,7,8-tetrahydro-5-[2-phthalazinyl) hydrazono]-1-naphthalenyl}oxy)propyl]dimethyl ammonium iodide. A mixture of 1.96g of 1-hydrazinophthalazine hydrochloride and 4.47g of D,L-(1,1-dimethylethyl)[2-hydroxy-3-({5,6,7,8-tetrahydro-5-oxo-1-naphthalenyl}oxy)-propyl] dimethyl ammonium iodide in 20ml of ethanol was refluxed for 18 hours. The solvent was evaporated, and the residue was treated with dilute sodium bicarbonate solution. The solid was collected and washed with water and dried to afford 5.80g (98.5%) of yellow powder, mp. 187°–190° dec. Recrystallization of the product from methanol-methylene chloride (1:1) gave yellow crystals, mp. 197°–198° dec.

Anal. Calcd. for $C_{27}H_{36}IN_5O_2$: C, 55.01; H, 6.16; I, 21.53; N, 11.88. Found: C, 55.14; H, 6.25; I, 21.60; N, 11.92.

EXAMPLE 5

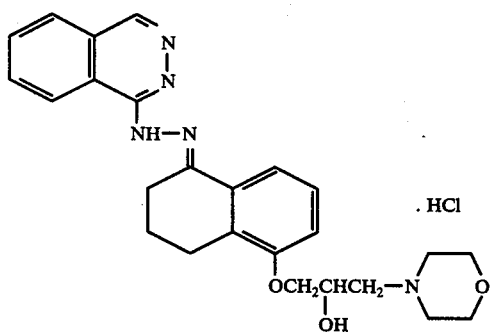

. HCl

D,L-5-{[3-morpholino]-2-hydroxypropoxy}-3,4-dihydro-1(2H)-naphthalenone (1-phthalazinyl)hydrazone hydrochloride. A mixture of 4.51g of 1-hydrazinophthalazine hydrochloride and 7.0g of 3,4-dihydro-5-[3-(4-morpholinyl)-2-hydroxypropoxy]-1(2H)-naphthalenone in 50ml of ethanol was refluxed for 18 hours. The starting materials slowly dissolved and a new precipitate formed. The solid was collected and dried to yield 10.7g (96.4%) of yellow powder, mp. 244°–246° dec.

Anal. Calcd. for $C_{25}H_{29}N_5O_3 \cdot HCl$: C, 62.04; H, 6.25; N, 14.47; Cl, 7.33. Found: C, 62.03; H, 6.27; N, 14.53; Cl, 7.49.

We claim:

1. A compound of the formula:

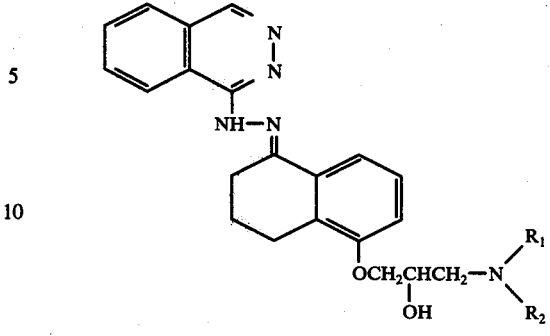

wherein $R_1$ is hydrogen or alkyl of 1–6 carbon atoms, $R_2$ is alkyl of 1–6 carbon atoms, and the pharmaceutically acceptable acid addition salts, and N-oxides.

2. A compound according to claim 1 in which $R_2$ is branched alkyl of 3–6 carbon atoms.

3. The compound according to claim 1 which is L-5-{[3-(1,1-dimethylethyl)amino]-2-hydroxypropoxy}-3,4-dihydro-1(2H)-naphthalenone (1-phthalazinyl)-hydrazone.

4. A compound according to claim 1 in which D,L-5-{[3-(1,1-dimethylethyl)amino]-2-hydroxypropoxy}-3,4-dihydro-1(2H)-naphthalenone (1-phthalazinyl)-hydrazone and its hydrochloride salt.

5. A compound according to claim 1 which is D-5-{[3-(1,1-dimethylethyl)amino]-2-hydroxypropoxy}-3,4-dihydro-1(2H)-naphthalenone (1-phthalazinyl)-hydrazone and its hydrochloride salt.

6. The compound according to claim 1 which is D,L-(1,1-dimethylethyl)[2-hydroxy-3-({5,6,7,8-tetrahydro-5-[2-phthalazinyl)hydrazono]-1-napththalenyl}oxy)-propyl]dimethyl ammonium iodide.

* * * * *